United States Patent [19]

Dean et al.

[11] Patent Number: 5,932,189

[45] Date of Patent: *Aug. 3, 1999

[54] CYCLIC PEPTIDE SOMATOSTATIN ANALOGS

[75] Inventors: Richard T. Dean, Bedford; William McBride, Manchester; John Lister-James, Bedford, all of N.H.

[73] Assignee: Diatech, Inc., Londonberry, N.H.

[*] Notice: This patent is subject to a terminal disclaimer.

[21] Appl. No.: 08/282,980

[22] Filed: Jul. 29, 1994

[51] Int. Cl.$^6$ .............................. A61K 51/00; A61M 36/14
[52] U.S. Cl. ...................... 424/1.69; 424/1.11; 424/1.65; 424/9.1; 530/311; 530/317
[58] Field of Search .................................. 424/1.11, 1.65, 424/1.69, 9.1, 9.3, 9.4, 9.5, 9.6; 530/300, 311, 317, 333, 334, 338; 534/7, 10–16

[56] References Cited

U.S. PATENT DOCUMENTS

| | | | |
|---|---|---|---|
| 4,235,886 | 11/1980 | Freidlinger . | |
| 4,366,148 | 12/1982 | Szabo et al. | 424/177 |
| 4,485,101 | 11/1984 | Coy et al. . | |
| 4,611,054 | 9/1986 | Freidlinger . | |
| 4,612,366 | 9/1986 | Nutt . | |
| 4,853,371 | 8/1989 | Coy et al. . | |
| 4,871,717 | 10/1989 | Coy et al. . | |
| 4,904,642 | 2/1990 | Coy et al. . | |
| 5,073,541 | 12/1991 | Taylor et al. . | |
| 5,382,654 | 1/1995 | Lyle et al. | 530/311 |
| 5,462,926 | 10/1995 | Coy et al. | 514/16 |
| 5,556,939 | 9/1996 | Flanagan et al. | 530/311 |
| 5,620,675 | 4/1997 | McBride et al. | 424/1.69 |
| 5,632,969 | 5/1997 | Flanagan et al. | 422/1.69 |

FOREIGN PATENT DOCUMENTS

| | | |
|---|---|---|
| 113029 | 7/1984 | European Pat. Off. . |
| 184622 | 7/1986 | European Pat. Off. . |
| 389180 | 9/1990 | European Pat. Off. . |
| 450480 | 10/1991 | European Pat. Off. . |
| 2225579 | 6/1990 | United Kingdom . |
| 9109056 | 6/1991 | WIPO . |
| WO 92/13554 | 8/1992 | WIPO . |

OTHER PUBLICATIONS

Spanevello et al (1991), Tetrahedron Letters vol. 32, No. 36, pp. 4675–4678, "Synthesis of Novel, Highly Potent Cyclic—Hexapeptide Analogs of Somatostatin. Potential Application of Orthogonal Protection for Affinity Chromatography".

Bomanji et al., (1992) *J. Nucl. Med.*, 33: pp. 1121–1124.
Bakker et al., (1991), *J. Nucl. Med.*, 32: pp. 1184–1189.
Bakker et al, (1990), *J. Nucl. Med.*, 31: pp. 1501–1509.

*Primary Examiner*—José G. Dees
*Assistant Examiner*—Dameron Jones
*Attorney, Agent, or Firm*—Patricia A. McDaniels; Kevin E. Noonan

[57] ABSTRACT

This invention relates to therapeutic reagents and peptides, including radiotherapeutic reagents and peptides, and radiodiagnostic reagents and peptides. Specifically, the invention relates to cyclic peptide derivatives and analogs of somatostatin, and embodiments of such peptides radiolabeled with a radioisotope, as well as methods for using such peptides for radiodiagnostic and radiotherapeutic purposes.

23 Claims, No Drawings

CYCLIC PEPTIDE SOMATOSTATIN ANALOGS

BACKGROUND OF THE INVENTION

1. Field of the Invention

This invention relates to therapeutic agents and peptides, radiotherapeutic agents and peptides, and radiodiagnostic agents and peptides. Specifically, the invention relates to cyclic peptide derivatives and analogues of somatostatin, and embodiments of such peptides labeled with radioisotopes of iodine.

2. Description of the Prior Art

Somatostatin is a tetradecapeptide that is endogenously produced by the hypothalamus and pancreas in humans and other mammals. The peptide has the formula:

Formula I

SEQ ID NO.:1

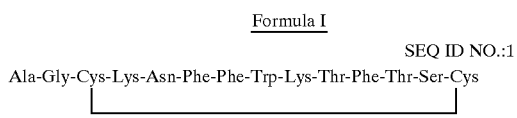

(Single letter abbreviations for amino acids can be found in G. Zubay, *Biochemistry* (2d ed.), 1988, (MacMillan Publishing: New York), p.33). This peptide exerts a wide variety of biological effects in vivo. It is known to act physiologically on the central nervous system, the hypothalamus, the pancreas, and the gastrointestinal tract.

Somatostatin inhibits the release of insulin and glucagon from the pancreas, inhibits growth hormone release from the hypothalamus, and reduces gastric secretions. Thus, somatostatin has clinical and therapeutic applications for the alleviation of a number of ailments and diseases, both in humans and other animals. Native somatostatin is of limited utility, however, due to its short half-life in vivo, where it is rapidly degraded by peptidases. For this reason, somatostatin analogues having improved in vivo stability have been developed in the prior art.

Freidinger, U.S. Pat. No. 4,235,886 disclose cyclic hexapeptide somatostatin analogues useful in the treatment of a number of diseases in humans.

Coy and Murphy, U.S. Pat. No. 4,485,101 disclose synthetic dodecapeptide somatostatin analogues.

Freidinger, U.S. Pat. No. 4,611,054 disclose cyclic hexapeptide somatostatin analogues useful in the treatment of a number of diseases in humans.

Nutt, U.S. Pat. No. 4,612,366 disclose cyclic hexapeptide somatostatin analogues useful in the treatment of a number of diseases in humans.

Coy et al., U.S. Pat. No. 4,853,371 disclose synthetic octapeptide somatostatin analogues.

Coy and Murphy, U.S. Pat. No. 4,871,717 disclose synthetic heptapeptide somatostatin analogues.

Coy et al., U.S. Pat. No. 4,904,642 disclose synthetic octapeptide somatostatin analogues.

Taylor et al., U.S. Pat. No. 5,073,541 disclose a method of treating small cell lung cancer.

Brady, European Patent Application No. 83111747.8 discloses dicyclic hexapeptide somatostatin analogues useful in the treatment of a number of human diseases.

Bauer et al., European Patent Application No. 85810617.2 disclose somatostatin derivatives useful in the treatment of a number of human diseases.

Eck and Moreau, European Patent Application No. 90302760.5 disclose therapeutic octapeptide somatostatin analogues.

Coy and Murphy, International Patent Application Serial No. PCT/US90/07074 disclose somatostatin analogues for therapeutic uses.

Schally et al., European Patent Application Serial No. EPA 911048445.2 disclose cyclic peptides for therapeutic use.

Bodgen and Moreau, International Patent Application Serial No. PCT/US92/01027 disclose compositions and methods for treating proliferative skin disease.

Somatostatin exerts its effects by binding to specific receptors expressed at the cell surface of cells comprising the central nervous system, the hypothalamus, the pancreas, and the gastrointestinal tract. These high-affinity somatostatin binding sites have been found to be abundantly expressed at the cell surface of most endocrine-active tumors arising from these tissues. Expression of high-affinity binding sites for somatostatin is a marker for these tumor cells, and specific binding with somatostatin can be exploited to locate and identify tumor cells in vivo.

Methods for radiolabeling somatostatin analogues that have been modified so as to contain a tyrosine amino acid (Tyr or Y) are known in the prior art.

Albert et al., UK Patent Application 8927255.3 disclose radioimaging using somatostatin derivatives such as octreotide labeled with $^{123}$I.

Bakker et al., 1990, J. Nucl. Med. 31:1501–1509 describe radioactive iodination of a somatostatin analog and its usefulness in detecting tumors in vivo.

Bakker et al., 1991, J. Nucl. Med. 32:1184–1189 teach the usefulness of radiolabeled somatostatin for radioimaging in vivo.

Bomanji et al., 1992, J. Nucl. Med. 33:1121–1124 describe the use of iodinated (Tyr-3) octreotide for imaging metastatic carcinoid tumors.

The use of chelating agents for radiolabeling proteins are known in the prior art, and methods for labeling peptides with Tc-99m are disclosed in co-pending U.S. patent applications Ser. Nos. 07/902,935 now U.S. Pat. No. 5,716,596, 08/092,355, and 08/095,760 now U.S. Pat. No. 5,620,675, and PCT International Applications PCT/US93/06029, which are hereby incorporated by reference.

SUMMARY OF THE INVENTION

The present invention provides somatostatin analogues that are cyclic peptides for therapeutic applications, including radiotherapeutic applications, and diagnostic applications, including radiodiagnostic applications, in particular scintigraphic imaging applications. Distinct from native somatostatin and somatostatin analogues known in the prior art, the cyclic peptides of the invention do not comprise a disulfide bond. The invention also provides cyclic peptide reagents comprised of the cyclic peptide somatostatin analogues of the invention, wherein such peptides are covalently linked to a moiety which modifies the pharmacokinetics of the compound. The invention also provides radiolabeled cyclic peptides that are scintigraphic imaging agents, radiodiagnostic agents and radiotherapeutic agents. Radiotherapeutic agents of the invention comprise cyclic peptide reagents radiolabeled with a cytotoxic radioisotope, preferably iodine-125 or iodine-131. Methods for making and using such cyclic peptides, cyclic peptide reagents and radiolabeled embodiments thereof are also provided.

The invention provides cyclic peptides, each of which is a somatostatin analogue as a composition of matter comprising a somatostatin-receptor binding peptide having the formula:

Formula II
cyclo($A^4$-$B^1B^2B^3B^4$-$C^4$)
where $B^1$ is D- or L-Phe or D- or L-Tyr or D- or L-Nal or Ain or a substituted derivative thereof; B2 is D- or L-Trp or a substituted derivative thereof; $B^3$ is D- or L-Lys or Hly, Achxa, Amf, Aec, Apc, Aes, Aps or a substituted derivative thereof; $B^4$ is Thr, Ser, Val, Phe, Ile, Abu, Nle, Leu, Nva or Aib; $C^4$ is an L-a-amino acid wherein the sidechain is covalently linked to an amino acid or amino acid amide, or a mono- or oligosaccharide comprising from 2 to about 10 saccharide residues, or a polyoxanion, a thiol, an hydroxyl, a sulfonyl or a sulfonamide, or a peptide comprising from 2 to about 10 amino acid residues, wherein the carboxyl terminus of the peptide is a carboxylic acid or amide; and $A^4$ is a lipophilic D-amino acid or a lipophilic L-($\alpha$-N-alkyl) amino acid or L-proline or substituted derivatives thereof. This moiety is a cyclic peptide moiety, where the amino terminus of the $A^4$ residue is covalently linked with the carboxyl terminus of the $C^4$ residue. In a preferred embodiment, $B^1$ is phenylalanine or tyrosine, $B^2$ is D-tryptophan, $B^3$ is lysine and $B^4$ is threonine or valine. In a preferred embodiment, the $C^4$ sidechain is covalently linked to an amino acid or amide or a peptide comprised of two to ten amino acids.

In certain embodiments of the somatostatin receptor-binding peptides provided by the invention, the sidechain of $C^4$ is covalently linked to an amino acid or amino acid amide, or a mono- or oligosaccharide comprising from 2 to about 10 saccharide residues, or a polyoxanion, a thiol, an hydroxyl, a sulfonyl or a sulfonamide, or a peptide comprising from 2 to about 10 amino acid residues, wherein the carboxyl terminus of the peptide is a carboxylic acid or amide, said covalent linkage via a bivalent linking group selected from the group consisting of a sulfur atom, an oxygen atom, an amine or substituted amine, or —HNO— —$CR_2$—$CR_2$—, —$CR_2$—O—, —$CR_2$—S—, —$CR_2$—C(O)—, —C(O)—$CR_2$—, —O—$CR_2$—, —S—$CR_2$—, —NRC(O)—, —$CR_2$—SO—, —SO—$CR_2$—, —COO—, —$NHSO_2$—, —$SO_2$—NH—, —SC(O)—, —C(O)S—, —C≡C—, —CR=CR—, and —C(O)NR—, wherein each R is independently H or lower alkyl, and two geminal R groups may be taken together as a lower alkylidene. In a preferred embodiment, $B^1$ is phenylalanine or tyrosine, $B^2$ is D-tryptophan, $B^3$ is lysine and $B^4$ is threonine or valine.

In other embodiments of the somatostatin receptor-binding peptides provided by the invention, the sidechain of $C^4$ is covalently linked to an amino acid or amino acid amide, or a peptide comprising from 2 to about 10 amino acid residues, wherein the carboxyl terminus of the peptide is a carboxylic acid or an amide, said covalent linkage via a thioether group. In a preferred embodiment, $B^1$ is phenylalanine or tyrosine, $B^2$ is D-tryptophan, $B^3$ is lysine and $B^4$ is threonine or valine.

In further embodiments of the cyclic somatostatin receptor-binding peptides provided by the invention, the sidechain of $C^4$ is —$(CH_2)_nSR^1$, where n is an integer from 1–4 and $R^1$ is H, lower alkyl, substituted alkyl, hydroxyalkyl, or alkoxyalkyl. In a preferred embodiment, $R^1$ is —$CH_2COR^2$, where $R^2$ is an amino acid or amino acid amide or a peptide comprising from 2 to about 10 amino acid residues, wherein the carboxyl terminus of the peptide is a carboxylic acid or an amide. In another preferred embodiment, $B^1$ is phenylalanine or tyrosine, $B^2$ is D-tryptophan, $B^3$ is lysine and $B^4$ is threonine or valine.

Somatostatin receptor-binding agents comprising multimers of the cyclic somatostatin receptor-binding peptides of the invention are also provided. Thus, the invention provides a composition of matter comprising a somatostatin receptor-binding peptide having the formula:
Formula III
$(Cyclo(A^4$-$B^1B^2B^3B^4$-$C^4))_m$
where m is an integer from 2 to 6; $B^1$ is D- or L-Phe or D- or L-Tyr or D- or L-Nal or Ain or a substituted derivative thereof; $B^2$ is D- or L-Trp or a substituted derivative thereof; $B^3$ is D- or L-Lys or Hly, Achxa, Amf, Aec, Apc, Aes, Aps or a substituted derivative thereof; $B^4$ is Thr, Ser, Val, Phe, Ile, Abu, Nle, Leu, Nva or Aib; $C^4$ is an L-$\alpha$-amino acid wherein the sidechain is —$(CH_2)_nSR^2$, where n is an integer from 1–4 and $R^2$ is a bond covalently linking two somatostatin receptor binding peptides, or wherein $R^2$ is a polyvalent linking moiety that is covalently linked to from 2 to about 6 of the somatostatin receptor-binding peptides to form a multimeric polyvalent somatostatin receptor binding agent; and $A^4$ is a lipophilic D-amino acid or a lipophilic L-($\alpha$-N-alkyl) amino acid or L-proline or substituted derivatives thereof. In a preferred embodiment, $B^1$ is phenylalanine or tyrosine, $B^2$ is D-tryptophan, $B^3$ is lysine and $B^4$ is threonine or valine.

The invention also provides pharmaceutical compositions comprising the somatostatin receptor-binding peptides of the invention in a pharmaceutically acceptable carrier.

The somatostatin analogues of the invention are therapeutically useful in the alleviation of diseases or other ailments in humans or other animals. The invention provides a method for alleviating somatostatin-related diseases in animals, preferably humans, comprising administering a therapeutically effective amount of the somatostatin analogues of the invention to the animal. In preferred embodiments, the amount of the somatostatin analogue administered is from about 0.1 to about 50 mg/kg body weight/day.

Another aspect of the present invention provides reagents for preparing radiotherapeutic and radiodiagnostic radiopharmaceuticals, including preferably scintigraphic imaging agents. Each such reagent is comprised of a peptide that is somatostatin analogue covalently linked to a radiolabel-binding moiety.

Loss of biological activity can occur in vivo using native somatostatin, or to any somatostatin analogue having a disulfide bond. Thus, the peptides of the present invention are per se advantageous as somatostatin analogues over native somatostatin or somatostatin analogues comprising a disulfide bond because they do not comprise such an unstable disulfide bond and hence are intrinsically more stable and resistant to chemical oxidation.

It is an advantage of the somatostatin analogues provided by this invention that the cyclic covalent linkage acts to protect the peptide from degradation by exopeptidases. Further, the cyclic structure confers a degree of conformational rigidity to the peptide that can act to enhance binding of the peptide to its biological target (i.e., the somatostatin receptor).

Many of the somatostatin receptor-binding peptides known heretofore have been found to have poor bioavailability as therapeutic agents and poor biodistribution as diagnostic agents due to unsuitable pharmacokinetics, such as too rapid uptake by the liver in vivo. It is another advantage of the somatostatin receptor-binding peptides of the present invention that their high in vivo stability is combined with pharmacokinetics better suited to use as pharmaceuticals.

The cyclic peptides of the invention may also be comprised of a polyvalent linking moiety. Polyvalent linking moieties of the invention are comprised of at least 2 identical linker functional groups capable of covalently bonding to somatostatin analogue cyclic peptides or radiolabel-binding moieties or both. Preferred linker functional groups are primary or secondary amines, hydroxyl groups, carboxylic acid groups or thiol-reactive groups. In preferred embodiments, the polyvalent linking moieties are comprised of bis-succinimidylmethylether (BSME), 4-(2,2-dimethylacetyl)benzoic acid (DMBA), N-(2-(N',N'-bis(2-succinimidoethyl)amioethyl))-$N^6$,$N^9$-bis(2-methyl-2-mercapto-propyl)-6,9-diazanonanamide (BAT-BS), tris(succinimidylethyl)amine (TSEA), bis-succinimidohexane (BSH), 4-(O—$CH_2$CO—Gly-Gly-Cys.amide)-2-methylpropiophenone (ETAC), tris(acetamidoethyl)amine, bis-acetamidomethyl ether, bis-acetamidoethyl ether, α,ε-bis-acetyllysine, lysine and 1,8-bis-acetamido-3,6-dioxaoctane, or derivatives thereof.

Specific preferred embodiments of the present invention will become evident from the following more detailed description of certain preferred embodiments and the claims.

DETAILED DESCRIPTION OF THE INVENTION

The present invention provides cyclic peptides that are somatostatin analogues and that are not comprised of a disulfide bond. Such somatostatin analogues thereby possess increased in vivo stability compared with native somatostatin or somatostatin analogues that comprise a disulfide bond. These cyclic peptides are themselves therapeutic agents for alleviating diseases and other ailments in animals including humans.

Also provided by the invention are cyclic peptides that may be radioiodinated or radioastatinated and which are thereby useful in radiotherapeutic and radiodiagnostic applications.

The invention provides a method for using the somatostatin analogues of the invention to alleviate diseases or other ailments in animals, preferably humans. These diseases and ailments include but are not limited to diabetes and diabetes-related retinopathy, cirrhosis of the liver and hepatitis infection, bleeding ulcers and other gastrointestinal bleeding, pancreatitis, central nervous system disorders, endocrine disorders, Alzheimer's disease, acromegaly and other diseases and disorders related to the production of inappropriate levels of growth hormone in vivo, and cancer, particularly those cancers whose growth is dependent or influenced by growth hormone or somatostatin production. Dosages of the somatostatin analogues provided by the invention may be the same as those dosages of native somatostatin routinely used for treatment of the above or other diseases, or less of the compounds of the invention may be administered due to their longer in vivo half-life.

Each somatostatin receptor-binding cyclic peptide-containing embodiment of the invention is comprised of a sequence of amino acids. The term amino acid as used in this invention is intended to include all L- and D- amino acids, naturally occurring and otherwise. Reagents comprising somatostatin receptor-binding peptides provided by the invention include but are not limited to the following illustrative examples of the peptide embodiments of the invention:

SEQ ID NO:2 cyclo.(N—$CH_3$)F.YW$_D$KV.Hcy
cyclo.(N—$CH_3$)F.YW$_{DD}$KV.Hcy($CH_2$CO.K(ε-K)GC.amide)
cyclo.(N-$CH_3$)F.YW$_D$KV.Hcy($CH_2$CO.C$_{Acm}$GC$_{Acm}$.amide)
cyclo.(N—$CH_3$)F.YW$_D$.KV.Hcy($CH_2$CO.CGC.amide)
cyclo.(N—$CH_3$)F.YW$_D$KV.Hcy($CH_2$CO.CGC)
cyclo.(N—$CH_3$)F.YW$_D$KV.Hcy($CH_2$CO.(ε-K)GC.amide)
cyclo.(N—$CH_3$)F.YW$_D$KV.Hcy($CH_2$CO.GGC.amide)
cyclo(N—Me)FYW$_D$KV.Hcy($CH_2$CO.CGCE.amide)
cyclo.(N—$CH_3$)FYW$_D$KV.Hcy($CH_2$CO.KKKKK(ε-K)GC.amide)
cyclo.(N—$CH_3$)FYW$_D$KV.Hcy($CH_2$CO.GGCK.amide)
cyclo.(N—$CH_3$)FYW$_D$.KV.Hcy($CH_2$CO.(ε-K)GCK.amide)
cyclo.(N—Me)FYW$_D$KV.Hcy($CH_2$CO.GGCR.amide)
cyclo.(N—Me)FYW$_D$KV.Hcy($CH_2$CO.GGCR.amide)
cyclo.(N—Me)FYW$_D$KV.Hcy($CH_2$CO.(ε-K)KC.amide)
cyclo.(N—Me)FYW$_D$KV.Hcy($CH_2$CO.GGCKK.amide)
cyclo.(N—Me)FYW$_D$KV.Hcy($CH_2$CO.GGC.Orn.amide)
cyclo.(N—Me)FYW$_D$KV.Hcy($CH_2$CO.GGC.Orn.DOrn..amide)
cyclo.(N—Me)FYW$_D$KV.Hcy($CH_2$CO.K(ε-K)KCK.amide)
cyclo.(N—Me)FYW$_D$KV.Hcy($CH_2$CO.(ε-K)GCKK.amide)
cyclo.(n—$CH_3$)FYW$_D$KV.Hcy($CH_2$COKKC.amide)
cyclo.(N—$CH_3$)FYW$_D$KV.Hcy($CH_2$COKKCK.amide)
cyclo.(N—$CH_3$)FYW$_D$KV.Hcy($CH_2$COGGCKKK.amide)
cyclo.(N—$CH_3$)FYW$_D$KV.Hcy$CH_2$CO.GGCRR.amide
cyclo.(N—$CH_3$)FYW$_D$KV.Hcy.$CH_2$CO.GGCRK.amide
cyclo.(N—$CH_3$)FYW$_D$KV.Hcy.$CH_2$CO.GGCRD.amide
cyclo.(N—$CH_3$)FYW$_D$KV.Hcy$CH_2$CO.(ε-K)DCK.amide
cyclo.(N—$CH_3$)FYW$_D$KV.Hcy$CH_2$COGGC.Orn.amide
cyclo.(N—$CH_3$)FYW$_D$KV.Hcy($CH_2$CO.GGCKDKD.amide)
cyclo.(N—$CH_3$)FYW$_D$KV.Hcy$CH_2$CO.GGCKD.amide
cyclo.(N—$CH_3$)FYW$_D$KV.Hcy$CH_2$CO.GGCKDK.amide
cyclo.(N—$CH_3$)FYW$_D$KV.Hcy$CH_2$CO.(ε-K)GCKKK.amide
cyclo.(N—$CH_3$)FYW$_D$KV.Hcy($CH_2$CO.(β-Dap)GCK.amide
cyclo.(N—$CH_3$)FYW$_D$KV.Hcy($CH_2$CO.(δ-Orn)GCK.amide)
cyclo.(N—$CH_3$)FYW$_D$KV.Hcy($CH_2$CO.(ε-K)GCRK.amide)
cyclo.(N—$CH_3$)FYW$_D$KV.Hcy($CH_2$CO.(ε-K)GCR.amide)
cyclo.(N—$CH_3$)FYW$_D$KVC SEQ ID NO:3
cyclo.(N—$CH_3$)FYW$_D$KT.Hcy SEQ ID NO:4
cyclo.PYW$_D$KV.Hcy SEQ ID NO:5
cyclo.(N—$CH_3$)FYW$_D$KV.Hcy($CH_2$CO.(γ-Dab)GCK.amide)
cyclo.(N—$CH_3$)FYW$_D$KV.Hcy($CH_2$CO.GRCK.amide)
cyclo.(N—$CH_3$)FYW$_D$KV.Hcy($CH_2$CO.KRC.amide)
cyclo.(N—$CH_3$)FYW$_D$KV.Hcy($CH_2$CO.GKCR.amide)
cyclo.(N—$CH_3$)FYW$_D$KV.Hcy($CH_2$CO.RRC.amide)
cyclo.(N—$CH_3$)FYW$_D$KV.Hcy($CH_2$CO.GGCE.amide)
cyclo.(N—$CH_3$)FYW$_D$KV.Hcy($CH_2$CO.GGC.Apc.amide)
cyclo.(N—$CH_3$)S(Bn)YW$_D$KV.Hcy
cyclo.PYW$_D$KV.Hcy($CH_2$CO.GGCK.amide)
cyclo.(NMe)FW$_D$KVC($CH_2$CO.GGCK.amide)

cyclo.(NMe)FW$_D$KT.Hcy(CH$_2$CO.GGCK.amide)
cyclo.(N—CH$_3$)FYW$_D$KV.Hcy(CH$_2$CO.RKC.amide)
cyclo.(N—CH$_3$)S(Bn)YW$_D$KV.Hcy (CH$_2$CO.GGCK.amide)
cyclo.(N—CH$_3$)FYW$_D$KV.Hcy(CH$_2$CO.GKCK.amide)
cyclo.(N—CH$_3$FYW$_D$KV.Hcy(CH$_2$CO.KGCK.amide)
cyclo.(N—CH$_2$)FYW$_D$KV.Hcy(CH$_2$CO.KGGCK.amide)
cyclo.(N—CH$_2$)FYW$_D$KV.Hcy(CH$_2$CO.KGGC.amide)
cyclo.(N—CH$_3$)FYW$_D$KV.Hcy(CH$_2$CO.GGGCK.amide)
cyclo.(N—CH$_3$)FYW$_D$KV.Hcy(CH$_2$CO.RGGC.amide)
cyclo.(N—CH$_3$)FYW$_D$KV.Hcy(CH$_2$CO.SSC.amide)
cyclo.(N—CH$_3$)FYW$_D$KV.Hcy(CH$_2$CO.SSCK.amide)
cyclo.(N—CH$_3$)FYW$_D$KV.Hcy(CH$_2$CO.($\beta$-Dap)KCK.amide)
cyclo.(N—CH$_3$)FYW$_D$KV.Hcy(CH$_2$CO.($\beta$-Dap)DCK.amide)
cyclo.(N—CH$_3$)FYW$_D$KV.Hcy(CH$_2$CO.($\beta$-Dap)KCD.amide)
cyclo.(N—CH$_3$)FYW$_D$KV.Hcy(CH$_2$CO.($\beta$-Dap)KCR.amide)
cyclo.(N—CH$_3$)FYW$_D$KV.Hcy(CH$_2$CO.($\beta$-Dap)GCR.amide)
cyclo.(N—CH$_3$)FYW$_D$KV.Hcy(CH$_2$CO.($\beta$-Dap)RCK.amide)
cyclo.(N—CH$_3$)FYW$_D$KV.Hcy(GK(—CH$_2$CO.)C.amide)
cyclo.(N—CH$_3$)FYW$_D$KV.Hcy(CH$_2$CO.GGCR.acid)
cyclo.(N—CH$_3$)FYW$_D$KV.Hcy(CH$_2$CO.GRC.amide)
cyclo.(N—CH$_3$)FYW$_D$KV.Hcy(CH$_2$CO.GGCK.acid)
cyclo.(N—CH$_3$)FYW$_D$KV.Hcy(CH$_2$CO.GKC.acid)
cyclo.(N—CH$_3$)FYW$_D$KV.Hcy(CH$_2$CO.GRC.acid)
cyclo.(N—CH$_3$)FYW$_D$KV.Hcy(CH$_2$CO.KKC.acid)
cyclo.(N—CH$_3$)FYW$_D$KV.Hcy (CH$_2$CO.CG.Dap.Dap.amide)
cyclo.(N—CH$_3$)FYW$_D$KV.Hcy(CH$_2$CO.($\delta$-Orn)GCR.amide)
cyclo.(N—CH$_3$)FYW$_D$KV.Hcy(CH$_2$CO.GNCR.amide)
cyclo.(N—CH$_3$)FYW$_D$KV.Hcy(CH$_2$CO.($\delta$-Orn)GCN.amide)
cyclo.(N—CH$_3$)FYW$_D$KV.Hcy (CH$_2$CO.GGC.Dap.amide)
cyclo.(Hyp.YW$_D$KV.Hcy) SEQ ID NO:7
cyclo.(Hyp.YW$_D$KV.Hcy(CH$_2$CO.GGCK.amide)
cyclo.(N—CH$_3$)FYW$_D$KV.Hcy(CH$_2$CO.($\gamma$-Dab)KCK.amide)
cyclo.(N—CH$_3$)FYW$_D$KV.Hcy(CH$_2$CO.($\gamma$-Dab)KCR.amide)
cyclo.(N—CH$_3$)FYW$_D$KV.Hcy(CH$_2$CO.($\delta$-Orn)KCK.amide).

As used herein, the following amino acids and amino acid analogues are intended to be represented by the following abbreviations: Ac is an acetyl group; ma is a mercaptoacetic acid group; Aca is 6-aminocaproic acid; Hcy is homocysteine; Hhc is homohomocysteine (3-mercaptopropylglycine); Pen is penicillamine; Mob is the sulfhydryl protecting group 4-methoxybenzyl; Acm is the sulfhydryl protecting group acetamidomethyl; Aib is aminoisobutyric acid; Nal is 2-naphthylalanine; Ain is 2-aminoindan-2-carboxylic acid; Hly is homolysine; Achxa is 4-amino-cyclohexylalanine; Amf is 4-aminomethyl-phenylalanine; Aec is S-(2-aminoethyl)cysteine; Apc is S-(3-aminopropyl) cysteine; Aes is O-(2-aminoethyl)serine; Aps is O-(3-aminopropyl)serine; Abu is 2-aminobutyric acid; Nva is norvaline; F$_D$ is D-phenylalanine; W$_D$ is D-tryptophan; Y$_D$ is D-tyrosine; Cpa is L-(4-chlorophenyl) alanine; Thp is 4-amino-tetrahydrothiopyran-4-carboxylic acid; D-Nal is D-2-naphthylalanine; Dpg is dipropylglycine; and Nle is norleucine. All naturally-occurring amino acids are abbreviated using standard abbreviations (which can be found in G. Zubay, *Biochemistry* (2d. ed.), 1988 (MacMillen Publishing: New York) p.33).

For the purposes of this invention, the naturally-occurring amino acids are characterized as lipophilic (alanine, isoleucine, leucine, methionine, phenylalanine, tyrosine, proline, tryptophan and valine, as well as S-alkylated derivatives of cysteine), hydrophilic (asparagine, glutamine, threonine, serine), acidic (glutamic acid and aspartic acid), basic (arginine, histidine and lysine). T(CH$_2$OH) represents a threoninol residue, wherein the carboxyl group of the amino acid is reduced to a primary alcohol, incorporated into the peptide using the procedure of Neugebauer et al. (1990, *Peptides: Proceedings of the 11th American Peptide Symposium*, pp. 1020–21). $\epsilon$-K is intended to represent a covalent linkage via the $\epsilon$-amino group on the sidechain of a lysine residue. $\delta$-represents an ornithine residue in which the $\delta$-amino group, rather than the typical $\alpha$-amino group, is covalently linked to the carboxyl group of the adjacent amino acid to form a peptide bond. $\gamma$-Dab represents a 2,4-diaminobutyric acid residue in which the $\gamma$-amino group is covalently linked to the carboxyl group of the adjacent amino acid to form a peptide bond. $\beta$-Dap represents a 1,3-diaminopropionic acid residue in which the $\beta$-amino group is covalently linked to the carboxyl group of the adjacent amino acid to form a peptide bond. (BMME) is bis-maleimidomethylether; (BSME) is bis-succinimidomethylether; and (DTPA) is diethylenetriaminepentaacetic acid. Hcy(alkyl group) is homocysteine, S-alkylated with the group in parenthesis.

The convention used herein of representing by underlining a covalent bond between atoms and groups of atoms, such as the amino terminus and carboxyl terminus resulting in the cyclic peptides of the invention, or similar representations of covalent bonding between the sidechain sulfur atom of a cysteine residue or derivative thereof and an amino terminal acyl group or other residue will also be understood by those with skill in the art. The use of the term "cyclo" herein is intended to indicate that the peptide is cyclized by formation of a covalent bond between the atoms of the amino terminal substituted or unsubstituted amino group and the carboxyl terminus of the peptide.

For the purposes of this invention the term "poly(N-carboxyalkyl)amine" in intended to describe a series of compounds exemplified by nitrilotriacetic acid, iminodiacetic acid, ethylenediaminetetraacetic acid (EDTA) and diethylenetriaminepentaacetic acid (DTPA).

For the purposes of this invention the term "polyoxyanion" is intended to encompass sulfates, phosphates, sulfonates, phosphonates, and like compounds.

Somatostatin analogue peptides of the present invention can be chemically synthesized in vitro. Peptides of the present invention can generally advantageously be prepared on a peptide synthesizer. The peptides of this invention can be synthesized wherein the radiolabel-binding moiety is covalently linked to the peptide during chemical synthesis in vitro, using techniques well known to those with skill in the art. Such peptides covalently-linked to the radiolabel-binding moiety during synthesis are advantageous because specific sites of covalent linkage can be determined.

The imaging reagents provided by the present invention can be used for visualizing organs such as the kidney for diagnosing disorders in these organs, and tumors, in particular gastrointestinal tumors, myelomas, small cell lung carcinoma and other APUDomas, endocrine tumors such as medullary thyroid carcinomas and pituitary tumors, brain tumors such as meningiomas and astrocytomas, and tumors of the prostate, breast, colon, and ovaries can also be imaged. In accordance with this invention, the radiolabeled peptide reagents are administered in a single unit injectable dose. The radiolabeled peptide reagents provided by the invention may be administered intravenously in any conventional medium for intravenous injection such as an aqueous saline medium, or in blood plasma medium. Generally, the unit dose to be administered has a radioactivity of about 0.01 mCi to about 100 mCi, preferably 1 mCi to 20 mCi. The solution to be injected at unit dosage is from about 0.01 mL to about 10 mL. After intravenous administration, imaging in vivo can take place in a matter of a few minutes. However, imaging can take place, if desired, in hours or even longer, after the radiolabeled peptide is injected into a patient. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The radiolabeled embodiments of the invention also have utility as surgical guides for identifying somatostatin receptor-expressing tumor tissue during surgery. For such use in radioisotope guided surgery, malignant tissue otherwise invisible to the surgeon can be recognized and excised during otherwise conventional surgery.

The somatostatin receptor-binding cyclic peptides of the invention may also be used clinically as therapeutic agents to promote regression of certain types of tumors, particularly those that express somatostatin receptors. The somatostatin analogue cyclic peptides of the invention can also be used to reduce the hormonal hypersecretion that often accompanies certain cancers, such as the APUDomas. Peptides of the invention used as therapeutic agents may be administered by any appropriate route, including intravenous, subcutaneous, intramuscular or by mouth, and in any acceptable pharmaceutical carrier, in doses ranging from about 0.1 to about 49 mg/kg body weight/day.

This invention also provides peptides radiolabeled with cytotoxic radioisotopes of iodine such as iodine-125 and iodine 131 that may be used for radiotherapy of certain tumors as described above. For this purpose, an amount of radioactive isotope from about 10 mCi to about 200 mCi may be administered via any suitable clinical route, preferably by intravenous injection.

The methods for making and labeling these compounds are more fully illustrated in the following Examples. These Examples illustrate certain aspects of the above-described method and advantageous results, and are shown by way of illustration and not limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with dicyclohexylcarbodiimide/ hydroxybenzotriazole or 2-(1H-benzotriazol-1-yl)-1,1,3,3-tetramethyluronium hexafluorophosphate/ hydroxybenzotriazole (HBTU/HOBT), and using p-hydroxymethyl henoxymethyl-polystyrene (HMP) resin or Sasrin™ resin for carboxyl-terminus acids or Rink amide resin for carboxyl-terminus amides.

Where appropriate, the following amino acid derivatives were synthesized. Homocysteine was prepared by alkaline hydrolysis of L-homocysteine lactone, or by reduction of L-homocystine using metallic sodium in liquid ammonia. Threoninol residues, wherein the carboxyl group of the amino acid is reduced to a primary alcohol, can be introduced into the peptides of the invention where appropriate using the procedure of Neugebauer et al. (1990, *Peptides: Proceedings of the 11th American Peptide Symposium*, pp. 1020–21). Fmoc.Hcy(Trt) and Fmoc.Pen(Trt) were prepared from the appropriate amino acids by tritylation with triphenylmethanol in TFA, followed by Fmoc derivitization as described by Atherton et al. (1989, *Solid Phase Peptide Synthesis*, IRL Press: Oxford). Fmoc.homohomocysteine (Trt) was prepared by reducing N,N-bis-Boc-glutamic acid-α-methyl ester with borane-THF, followed by mesylation and reaction with trityl-mercaptide, followed by removal of the Boc groups with $BF_3OEt_2$ in acetic acid, and then Fmoc derivitization as described above. phenyl-$CH_2$CHBrCOOH was prepared by treating phenylalanine (in a solution of water and TFA/saturated with NaBr) with sodium nitrite, followed by distillation to recover the pure product.

Where appropriate, 2-chloroacetyl, 2-bromoacetyl and 2-bromo-3-phenylpropionyl groups were introduced either by using the appropriate 2-halo acid as the last residue coupled during SPPS, or by treating the N-terminus free amino acid peptide bound to the resin with either 2-halo acid/ diisopropylcarbodiimide/N-hydroxysuccinimide/NMP or 2-halo acid anhydride/ diisopropylethylamine/NMP.

Where appropriate, thiol-containing peptides were reacted with chloroacetyl-containing, thiol-protected Tc-99m complexing moieties at pH 10 for 0.5–4 hours at room temperature, followed by acetic acid acidification and evaporation of the solution to give the corresponding peptide-sulfide adduct. Deprotection and purification were routinely performed as described to yield the chelator-peptide conjugate.

Where appropriate, BSME adducts were prepared by reacting single thiol-containing peptides (5 to 50 mg/mL in DMF buffered to pH 7 with N-methylmorpholine or N-ethylmorpholine, or 50 mM sodium phosphate buffer, pH 7–8, optionally containing 0.5 mM EDTA or DMF or THF or acetonitrile) with 0.5 molar equivalents of BMME (bis-maleimidomethylether) pre-dissolved in acetonitrile at room temperature for approximately 1–18 hours. The solution was concentrated and the product was purified by HPLC.

Where appropriate, TSEA adducts were prepared by reacting single thiol-containing peptide (at concentrations of 10 to 100 mg/mL peptide in DMF buffered to pH 7 with N-methylmorpholine or N-ethylmorpholine, or 5 to 50 mg/mL peptide in 50 mM sodium phosphate, pH 7–8, optionally containing 0.5 mM EDTA or DMF or THF or acetonitrile) with 0.33 molar equivalents of TMEA (tris(2-maleimidoethyl)amine) pre-dissolved in acetonitrile or DMF, with or without 1 molar equivalent of triethanolamine, at room temperature for approximately 1–18 h. Such reaction mixtures containing adducts were concentrated and the adducts were then purified using HPLC.

Where appropriate, the (DTPA) moiety can be introduced using the method of Bakker et al. (1991, Life Sci. 49:1583–1591, hereby incorporated by reference).

Where appropriate, peptide precursors were cyclized (between the amino- and carboxyl-termini) by reaction of the sidechain-protected, N-terminal free amine and C-terminal free acid with diphenylphosphorylazide.

Sasrin™ resin-bound peptides were cleaved using a solution of 1% TFA in dichloromethane to yield the protected peptide. Where appropriate, protected peptide precursors were cyclized between the amino- and carboxyl-termini by reaction of sidechain-protected, amino-terminal free amine and carboxyl-terminal free acid using diphenylphosphorylazide.

HMP or Rink amide resin-bound products were routinely cleaved and protected cyclized peptides deprotected using a solution comprised of trifluoroacetic acid (TFA), or TFA and methylene chloride, optionally comprising water, thioanisole, ethanedithiol, and triethylsilane or triisopropylsilane in ratios of 100:5:5:2.5:2, for 0.5–3 hours at room temperature. Where appropriate, products were re-S-tritylated in triphenolmethanol/TFA, and N-Boc groups re-introduced into the peptide using $(Boc)_2O$.

Resin-bound products were routinely cleaved using a solution of trifluoroacetic acid or trifluoroacetic acid and methylene chloride, optionally containing water, thioanisole, ethanedithiol, and triethylsilane, prepared in ratios of 100:5:5:2.5:2 for 0.5–3 h at room temperature. Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS) or by electrospray mass spectroscopy (ESMS).

Somatostatin analogues synthesized as provided herein, as well as the products of such synthesis identified by FABMS, are shown in Table I below.

cyclohexylalanine; Amf=4-aminomethyl-phenylalanine; Aec=S-(2-aminoethyl)cysteine; Apc=S-(3-aminopropyl)cysteine; Aes=O-(2-aminoethyl)serine; Aps=O-(3-aminopropyl)serine; Abu=2-aminobutyric acid; Nva=norvaline; $T(CH_2OH)$=threoninol (on which the carboxylic acid moiety has been reduced to a primary alcohol); $\epsilon$-K=a lysine residue in a peptide in which the peptide bond involves the $\epsilon$-amino group on the lysine sidechain rather than the $\alpha$-amino group; $\delta$-Orn=an ornithine residue in which the $\delta$-amino group, rather than the typical $\alpha$-amino group, is covalently linked to the carboxyl group of the adjacent amino acid to form a peptide bond; $\gamma$-Dab=a 2,4-diaminobutyric acid residue in which the $\gamma$-amino group is covalently linked to the carboxyl group of the adjacent amino acid to form a peptide bond; $\beta$-Dap=a 1,3-diaminopropionic acid residue in which the $\beta$amino group is covalently linked to the carboxyl group of the adjacent amino acid to form a peptide bond; (BMME)=bis-maleimidomethylether; (BSME)=bis-succinimidomethylether; (DTPA)=diethylenetriaminepentaacetic acid.

EXAMPLE 2

Inhibition of Binding of ($^{125}$I-Tyr$^{11}$)somatostatin-14 to AR42J Rat Pancreatic Tumor Cell Membranes The ability of various somatostatin analogues of the invention to bind to somatostatin receptors in vitro was demonstrated by assaying the ability of such analogues to inhibit binding of a radiolabeled somatostatin analogue to somatostatin receptor-containing cell membranes. The rat pancreatic tumor cell line AR42J which expresses the somatostatin receptor was cultured in Dulbecco's minimal essential media (DMEM) supplemented with 10% fetal bovine serum (FBS) and 8 mM glutamine in a humidified 5% $CO_2$ atmosphere at 37° C. in T-flasks. Harvested cells were

TABLE I

| Peptide | MH + FABMS |
|---|---|
| cyclo.CYW$_D$KVC SEQ ID NO: 8 | 783 |
| cyclo.(N—CH$_3$)F.YW$_D$KV.Hcy(CH$_2$CO.CGC.amide) | 1176 |
| cyclo.(N—CH$_3$)F.YW$_D$KV.Hcy(CH$_2$CO.CGC) | 1177 |
| cyclo.(N—CH$_3$)F.YW$_D$KV.Hcy(CH$_2$CO.($\epsilon$-K)GC.amide) | 1201 |
| cyclo.(N—CH$_3$)F.YW$_D$KV.Hcy(CH$_2$CO.GGC.amide) | 1129 |
| cyclo(N—CH$_3$)FFW$_D$KTFCC$_{Acm}$GC$_{Acm}$.amide) SEQ ID NO: 9 | 1609 |
| cyclo(N—CH$_3$)FYW$_D$KV.Hcy(CH$_2$COGGCK.amide) | 1258 |
| cyclo(N—CH$_3$)FYW$_D$KV.Hcy(CH$_2$CO($\epsilon$-K)GCK.amide) | 1329 |
| cyclo(N—CH$_3$)FYW$_D$KV.Hcy(CH$_2$COGGCR.amide) | 1285 |
| cyclo(N—CH$_3$)FYW$_D$KV.Hcy(CH$_2$CO($\epsilon$-K)KC.amide) | 1472 |
| cyclo(N—CH$_3$)FYW$_D$KV.Hcy(CH$_2$COGGC.Orn.amide) | 1244 |
| cyclo(N—CH$_3$)FYW$_D$KV.Hcy(CH$_2$CO($\beta$-Dap)KC.amide) | 1358 |
| cyclo.(N—CH$_3$)FYW$_D$KV.Hcy(CH$_2$CO.KKKKK($\epsilon$-K)GC.amide) | 1841 |

Single-letter abbreviations for amino acids can be found in G. Zubay, *Biochemistry* (2d. ed.), 1988 (MacMillen Publishing: New York) p.33; Ac=acetyl; Acm=acetamidomethyl; ma=mercaptoacetic acid; Mob=4-methoxybenzyl; Aca=6-aminocaproic acid; Hly=homolysine; Apc=L-(S-(3-aminopropyl)cysteine; F$_D$=D-phenylalanine; W$_D$=D-tryptophan; Y$_D$=D-tyrosine; Cpa=L-(4-chlorophenyl)alanine; Thp=4-amino-tetrahydrothiopyran-4-carboxylic acid; D-Nal=D-2-naphthylalanine; Dpg=dipropylglycine; Nle=norleucine; Hcy=homocysteine; Hhc=homohomocysteine; Pen=penicillamine; Aib=aminoisobutyric acid; Nal=2-naphthylalanine; D-Nal=D-2-naphthylalanine; Ain=2-aminoindan-2-carboxylic acid; Achxa=4-aminohomogenized in cold 50 mM Tris-HCl buffer (pH 7.4) and the homogenate then centrifuged at 39,000 g for 10 min at 4° C. Pellets were washed once with buffer and then resuspended in an ice-cold solution of 10 mM Tris-HCl (pH 7.4). Equal aliquots of this cell membrane preparation were incubated with ($^{125}$I-Tyr$^{11}$)somatostatin-14 (at a final concentration of 0.5 nM and 750,000 cpm/mL, at a specific activity of 2000 Ci/mmol, Amersham, Arlington Heights, Ill.) and peptide at a final concentration of from $10^{-11}$M to $10^{-6}$M in a solution of 50 mM HEPES (pH 7.4) containing 1% bovine serum albumin (BSA), 5 mM $MgCl_2$, Trasylol (200,000 International Units), bacitracin (0.02 mg/mL) and phenylmethylsulfonylfluoride (0.02 mg/mL) for 25 min at 30° C. Using a filtration manifold, this mixture was filtered through a polyethyleneimine-washed GC/F filter (Whatman, Maidstone, England), and the residue remaining on the filter washed thrice with 5 mL cold HEPES buffer. The filter and a sample of the filter washings were then counted in a gamma counter. To assess non-specific binding, the assay was performed in the presence of unlabeled somatostatin-14 at 200 nM. Data analysis including Hill plots of the data provided inhibition constants (see Bylund & Yamamura, "Methods of receptor binding", in *Methods in Neurotransmitter Receptor Analysis*, Yamamura et al., eds., Raven Press: New York, 1990).

These results are presented in the following Table. The data show that the peptides of the instant invention have a high affinity of binding for somatostatin receptors.

TABLE II

| Peptide | $K_i$ (nM) |
| --- | --- |
| cyclo.(N—CH$_3$)F.YW$_D$KV.Hcy SEQ ID NO: 3 | <0.01 |
| cyclo.(N—CH$_3$)F.YW$_D$KT.Hcy SEQ ID NO: 4 | 0.26 |
| cyclo.(N—CH$_3$)F.YW$_D$KV.Hcy(CH$_2$CO.GGCKK.amide) | 0.26 |
| cyclo.(N—CH$_3$)F.YW$_D$KV.Hcy(CH$_2$CO.GGCR.amide) | 0.29 |
| cyclo.(N—CH$_3$)F.YW$_D$KV.Hcy(CH$_2$CO.K(ε-K)GC.amide) | 0.65 |
| cyclo.(N—CH$_3$)F.YW$_D$KV.Hcy(CH$_2$CO.C$_{Acm}$GC$_{Acm}$.amide) | 0.79 |
| cyclo.(N—CH$_3$)F.YW$_D$KV.Hcy(CH$_2$CO.CGC.amide) | 1.5 |
| cyclo.(N—CH$_3$)F.YW$_D$KV.Hcy(CH$_2$CO.CGC) | 1.8 |
| cyclo.(N—CH$_3$)F.YW$_D$KV.Hcy(CH$_2$CO.(ε-K)GC.amide) | 2.0 |
| cyclo.(N—CH$_3$)F.YW$_D$KV.Hcy(CH$_2$CO.(ε-K)KC.amide) | 2.2 |
| cyclo.(N—CH$_3$)F.YW$_D$KV.Hcy(CH$_2$CO.GGC.amide) | 2.4 |
| cyclo.(N—CH$_3$)F.YW$_D$KV.Hcy(CH$_2$CO.GGCK.amide) | 2.5 |
| cyclo.(N—CH$_3$)F.YW$_D$KV.Hcy(CH$_2$CO.(ε-K)GCK.amide) | 4.2 |
| cyclo.(N—CH$_3$)F.YW$_D$KV.Hcy(CH$_2$CO.CGCE.amide) | 8.5 |

EXAMPLE 4

Localization and In Vivo Imaging of Somatostatin Receptor (SSTR)-Expressing Tumors in Rats In vivo imaging of somatostatin receptors expressed by rat tumor cells is performed essentially as described by Bakker et al. (1991, *Life Sciences* 49:1593–1601).

CA20948 rat pancreatic tumor cells, thawed from frozen harvested tumor brei, are implanted intramuscularly in a suspension of 0.05 to 0.1 mL/animal, into the right hind thigh of 6 week old Lewis rats. The tumors are allowed to grow to approximately 0.5 to 2 g, harvested, and tumor brei was used to implant a second, naive set of Lewis rats. Passaging in this fashion is repeated to generate successive generations of tumor-bearing animals. The tumor-bearing animals used for the in vivo studies are usually from the third to fifth passage and carried 0.2 to 2 g tumors.

For studies of the specificity of radiotracer localization in the tumors, selected animals are given an subcutaneous SSTR-blocking dose (4 mg/kg) of octreotide 30 minutes prior to injection of the radiotracer. (This protocol has been shown by Bakker et al. to result in a lowering of $^{111}$In-(DTPA)octreotide tumor uptake by 40%.)

Third- to fifth-passage CA20948 tumor-bearing Lewis rats are restrained and injected intravenously via the dorsal tail vein with a dose of 0.15–0.20 mCi $^{99m}$Tc-labeled peptide corresponding to 3 to 8 μg peptide in 0.2 to 0.4 mL.

At selected times, the animals are sacrificed by cervical dislocation and selected necropsy was performed. Harvested tissue samples are weighed and counted along with an aliquot of the injected dose in a gamma well-counter.

It should be understood that the foregoing disclosure emphasizes certain specific embodiments of the invention and that all modifications or alternatives equivalent thereto are within the spirit and scope of the invention as set forth in the appended claims.

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
      (A) LENGTH: 14 amino acids
      (B) TYPE: amino acid
      (D) TOPOLOGY: circular (ii) MOLECULE TYPE: peptide (ix) FEATURE:
      (A) NAME/KEY: Modified-site
      (B) LOCATION: 3..14
      (D) OTHER INFORMATION: /label= Disulfide bond
          /note= "A disulfide bond exists between the
          two sulfur atoms of the cysteine residues;

(xi) SEQUENCE DESCRIPTION: SEQ ID NO:1:

Ala Gly Cys Lys Asn Phe Phe Trp Lys Thr Phe Thr Ser Cys
   1           5                  10

(2) INFORMATION FOR SEQ ID NO:2:

(i) SEQUENCE CHARACTERISTICS:
      (A) LENGTH: 6 amino acids

```
            (B) TYPE: amino acid
            (D) TOPOLOGY: circular (ii) MOLECULE TYPE: peptide (ix) FEATURE:
            (A) NAME/KEY: Modified-site
            (B) LOCATION: 1..6
            (D) OTHER INFORMATION: /label= Cyclic
                  /note= "The amino terminus and carboxyl terminus
                  are linked by a covalent bond; the amino terminus
                  is substituted with a methyl group."

(ix) FEATURE:
            (A) NAME/KEY: Modified-site
            (B) LOCATION: 1..6
            (D) OTHER INFORMATION: /label= Variant residues
                  /note= "The Trp is in the D conformation; Xaa
                  is homocysteine."

(xi) SEQUENCE DESCRIPTION: SEQ ID NO:2:

Phe Tyr Trp Lys Val Xaa
     1               5

(2) INFORMATION FOR SEQ ID NO:3:

(i) SEQUENCE CHARACTERISTICS:
            (A) LENGTH: 6 amino acids
            (B) TYPE: amino acid
            (D) TOPOLOGY:circular (ii) MOLECULE TYPE: peptide (ix) FEATURE:
            (A) NAME/KEY: Modified-site
            (B) LOCATION: 1..6
            (D) OTHER INFORMATION: /label= Cyclic
                  /note= "The amino terminus and carboxyl terminus
                  are linked by a covalent bond; the amino terminus
                  is substituted with a methyl group."

(xi) SEQUENCE DESCRIPTION: SEQ ID NO:3:

Phe Tyr Trp Lys Val Cys
     1               5

(2) INFORMATION FOR SEQ ID NO:4:

(i) SEQUENCE CHARACTERISTICS:
            (A) LENGTH: 6 amino acids
            (B) TYPE: amino acid
            (D) TOPOLOGY:circular (ii) MOLECULE TYPE: peptide (ix) FEATURE:
            (A) NAME/KEY: Modified-site
            (B) LOCATION: 1..6
            (D) OTHER INFORMATION: /label= Cyclic
                  /note= "The amino terminus and carboxyl terminus
                  are linked by a covalent bond; the amino terminus
                  is substituted with a methyl group."

(ix) FEATURE:
            (A) NAME/KEY: Modified-site
            (B) LOCATION: 1..6
            (D) OTHER INFORMATION: /label= Variant residues
                  /note= "The Trp is in the D conformation; Xaa
                  is homocysteine."

(xi) SEQUENCE DESCRIPTION: SEQ ID NO:4:

Phe Tyr Trp Lys Thr Xaa
     1               5

(2) INFORMATION FOR SEQ ID NO:5:
```

(i) SEQUENCE CHARACTERISTICS:
        (A) LENGTH: 6 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION: 1..6
        (D) OTHER INFORMATION: /label= Cyclic
            /note= "The amino terminus and carboxyl terminus
            are linked by a covalent bond."

(ix) FEATURE:
        (A) NAME/KEY: Modified-site
        (B) LOCATION: 1..6
        (D) OTHER INFORMATION: /label= Variant residues
            /note= "The Trp is in the D conformation; Xaa
            is homocysteine."

(xi) SEQUENCE DESCRIPTION: SEQ ID NO:5:

Pro Tyr Trp Lys Val Xaa
   1               5

(2) INFORMATION FOR SEQ ID NO:6:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION: 1..6
        (D) OTHER INFORMATION: /label= Cyclic
            /note= "The amino terminus and carboxyl terminus
            are linked by a covalent bond; the amino terminus
            is substituted with a methyl group."

(ix) FEATURE:
        (A) NAME/KEY: Modified-site
        (B) LOCATION: 1..6
        (D) OTHER INFORMATION: /label= Variant residues
            /note= "The Trp is in the D conformation; Xaa
            is homocysteine; the serine hydroxyl is benzylated."

(xi) SEQUENCE DESCRIPTION: SEQ ID NO:6:

Ser Tyr Trp Lys Val Xaa
   1               5

(2) INFORMATION FOR SEQ ID NO:7:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION: 1..6
        (D) OTHER INFORMATION: /label= Cyclic
            /note= "The amino terminus and carboxyl terminus
            are linked by a covalent bond."

(ix) FEATURE:
        (A) NAME/KEY: Modified-site
        (B) LOCATION: 1..6
        (D) OTHER INFORMATION: /label= Variant residues
            /note= "The Trp is in the D conformation; the first
            Xaa is hydroxyproline; the second Xaa is homocysteine."

-continued

```
    (xi) SEQUENCE DESCRIPTION: SEQ ID NO:7:

Xaa Tyr Trp Lys Val Xaa
    1               5

(2) INFORMATION FOR SEQ ID NO:8:

(i) SEQUENCE CHARACTERISTICS:
        (A) LENGTH: 6 amino acids
        (B) TYPE: amino acid
        (D) TOPOLOGY: circular (ii) MOLECULE TYPE: peptide (ix) FEATURE:
        (A) NAME/KEY: Modified-site
        (B) LOCATION: 1..6
        (D) OTHER INFORMATION: /label= Cyclic
            /note= "The amino terminus and carboxyl terminus
            are linked by a covalent bond."

(ix) FEATURE:
        (A) NAME/KEY: Modified-site
        (B) LOCATION: 1..3
        (D) OTHER INFORMATION: /label= Variant residues
            /note= "The Trp is in the D conformation"

(xi) SEQUENCE DESCRIPTION: SEQ ID NO:8:

Cys Tyr Trp Lys Val Cys
    1               5

(2) INFORMATION FOR SEQ ID NO:9:

(i) SEQUENCE CHARACTERISTICS:
        (A) LENGTH: 10 amino acids
        (B) TYPE: amino acid
        (D) TOPOLOGY:circular (ii) MOLECULE TYPE: peptide (ix) FEATURE:
        (A) NAME/KEY: Modified-site
        (B) LOCATION: 1..7
        (D) OTHER INFORMATION: /label= Cyclic
            /note= "The amino terminus and carboxyl terminus
            are linked by a covalent bond."

(ix) FEATURE:
        (A) NAME/KEY: Modified-site
        (B) LOCATION: 1..3
        (D) OTHER INFORMATION: /label= Variant residues
            /note= "The Trp is in the D conformation."

(ix) FEATURE:
        (A) NAME/KEY: Modified-site
        (B) LOCATION: 8..10
        (D) OTHER INFORMATION: /label= Tc-99m-chelator
            /note= "The sidechain sulfur atoms of both Cys
            residues are each protected with an
            acetamidomethyl group"

(ix) FEATURE:
        (A) NAME/KEY: Modified-site
        (B) LOCATION: 10
        (D) OTHER INFORMATION: /label= Amide
            /note= "The carboxyl terminus is modified to an
            amide"

(xi) SEQUENCE DESCRIPTION: SEQ ID NO:9:

Phe Phe Trp Lys Thr Phe Cys Cys Gly Cys
    1               5                   10
```

What is claimed is:

1. A composition comprising a somatostatin receptor-binding peptide having a formula:

cyclo($A^4$-$B^1B^2B^3B^4$-$C^4$)

wherein $B^1$ is D- or L-Phe or D- or L-Tyr or D- or L-Nal or Ain or a substituted derivative thereof;

$B^2$ is D- or L-Trp or a substituted derivative thereof;

$B^3$ is D- or L-Lys or Hly, Achxa, Amf, Aec, Apc, Aes, Aps or a substituted derivative thereof;

$B^4$ is Thr, Ser, Val, Phe, Ile, Abu, Nle, Leu, Nva or Aib;

$C^4$ is an α-amino acid having a sidechain covalently linked to an amino acid, an amino acid amide, a monosaccharide, an oligosaccharide comprising from 2 to about 10 saccharide residues, a polyoxanion, a thiol, an hydroxyl, a sulfonyl, a sulfonamide, a second peptide comprising from 2 to about 10 amino acid residues and having a carboxyl terminal carboxylic acid, or a second peptide comprising from 2 to about 10 amino acid residues and having a carboxyl terminal amide; and $A^4$ is a lipophilic D-amino acid or a lipophilic L-(α-N-alkyl) amino acid or L-proline or a substituted derivative thereof;

wherein the peptide is cyclized through a covalent linkage between an α-amino terminus of residue $A^4$ and an α-carboxyl terminus of residue $C^4$.

2. The composition of claim 1, wherein the sidechain of residue $C^4$ is covalently linked through a bivalent linking group selected from the group consisting of:

a sulfur atom, an oxygen atom, an amine or substituted amine, —HNO—, —$CR_2$—$CR_2$—, —$CR_2$—O—, —$CR_2$—S—, —$CR_2$—C(O)—, —C(O)—$CR_2$—, —O—$CR_2$—, —S—$CR_2$—, —NRC(O)—, —$CR_2$—SO—, —SO—$CR_2$—, —COO—, —$NHSO_2$—, —$SO_2$—NH—, —SC(O)—, —C(O)S—, —C=C—, —CR=CR—, and —C(O)NR—, wherein each R is independently H or lower alkyl, and two geminal R groups may be taken together as a lower alkylidene.

3. The composition of claim 2, wherein the sidechain of residue $C^4$ is covalently linked through a thioether group to an amino acid, or to an amino acid amide, or to a second peptide comprising from 2 to about 10 amino acid residues and having a carboxyl terminal carboxylic acids or to a second peptide comprising from 2 to about 10 amino acid residues and having a carboxyl terminal amide.

4. The composition of claim 1, wherein $B^1$ is phenylalanine or tyrosine, $B^2$ is D-tryptophan, $B^3$ is lysine, and $B^4$ is threonine or valine.

5. A composition comprising a somatostatin receptor-binding peptide having a formula:

cyclo($A^4$-$B^1B^2B^3B^4$-$C^4$)

wherein $B^1$ is D- or L-Phe or D- or L-Tyr or D- or L-Nal or Ain or a substituted derivative thereof;

$B^2$ is D- or L-Trp or a substituted derivative thereof;

$B^3$ is D- or L-Lys or Hly, Achxa, Amf, Aec, Apc, Aes, Aps or a substituted derivative thereof;

$B^4$ is Thr, Ser, Val, Phe, Ile, Abu, Nle, Leu, Nva or Aib;

$A^4$ is a lipophilic D-amino acid or a lipophilic L-(α-N-alkyl) amino acid or

L-proline or a substituted derivative thereof;

$C^4$ is an Lα-amino acid having a sidechain

—$(CH_2)_n SR^1$ where n is an integer from 1–4 and $R^1$ is H, lower alkyl, substituted alkyl, hydroxyalkyl, or alkoxyalkyl;

wherein the peptide is cyclized through a covalent linkage between an α-amino terminus of residue $A^4$ and an α-carboxyl terminus of residue $C^4$.

6. The composition of claim 5, wherein $R^1$ is —$CH_2COR^2$, where $R^2$ is selected from the group consisting of an amino acids an amino acid amides a second peptide comprising from 2 to about 10 amino acid residues and having a carboxyl terminal carboxylic acids and a second peptide comprising from 2 to about 10 amino acid residues and having a carboxyl terminal amide.

7. The composition of claim 6, wherein $B^1$ is phenylalanine or tyrosine, $B^2$ is D-tryptophan, $B^3$ is lysine and $B^4$ is threonine or valine.

8. A composition comprising at least two somatostatin receptor-binding peptides having a formula:

(cyclo($A^4$-$B^1B^2B^3B^4$-$C^4$))$_m$ wherein $B^1$ is D- or L-Phe or D- or L-Tyr or D- or L-Nal or Ain or a substituted derivative thereof;

$B^2$ is D- or L-Trp or a substituted thereof;

$B^3$ is D- or L-Lys or Hly, Achxa, Amf, Aec, Apc, Aes, Aps or a substituted thereof;

$B^4$ is Thr, Ser, Val, Phe, Ile, Abu, Nle, Leu, Nva or Aib;

$A^4$ is a lipophilic α-amino acid or a lipophilic L-((α-N-alkyl) amino acid or L-proline or a substituted derivative thereof;

$C^4$ is an α-amino acid having a sidechain —$(CH_2)_n SR^2$ where n is an integer from 1-4 and $R^2$ is selected from the group consisting of a bond covalently linking said peptides and a polyvalent linking moiety covalently linked to said peptides;

m is an integer from 2 to 6;

and wherein each of said peptides is cyclized through a covalent linkage between an α-amino terminus of residue $A^4$ and an α-carboxyl terminus of residue $C^4$.

9. The composition of claim 8, wherein $B^1$ is phenylalanine or tyrosine, $B^2$ is D-tryptophan, $B^3$ is lysine and $B^4$ is threonine or valine.

10. The composition of claim 8, wherein the polyvalent linking moiety is selected from the group consisting of bis-succinimidylmethylether, 4-(2,2-dimethylacetyl)benzoic acid, N-(2-(N',N'bis(2-succinimido-ethyl)aminoethyl))-$N^6$, $N^9$-bis(2-methyl-2-mercapto-propyl)-6,9-diazanonanamide, tris(succinimidylethyl)amine, bis-succinimidohexane, 4-(O-$CH_2$CO-Gly-Gly-Cys.amide)-2-methylpropiophenone, tris(acetamidoethyl)amine, bis-acetamidomethyl ether, bis-acetamidoethyl ether, α,ε-bis-acetyllysine, lysine, 1,8-bis-acetamido-3,6-dioxa-octane, a derivative of bis-succinimidylmethylether, a derivative of 4-(2,2-dimethylacetyl)benzoic acid, a derivative of N-(2-(N',N'bis(2-succinimido-ethyl)aminoethyl))-$N^6$, $N^9$-bis(2-methyl-2-mercapto-propyl)-6,9-diazanonanamide, a derivative of tris(succinimidylethyl)amine, a derivative of bis-succinimidohexane, a derivative of 4-(O—$CH_2$CO—Gly-Gly-Cys.amide)-2-methylpropiophenone, a derivative of tris(acetamidoethyl)amine, a derivative of bis-acetamidomethyl ether, a derivative of bis-acetamidoethyl ether, a derivative of α,ε-bis-acetyllysine, a derivative of lysine and a derivative of 1,8-bis-acetamido-3,6-dioxa-octane.

11. A composition according to claims 1, 2, 3, 4, 5, 6, 7, 8, 9, or 10 further comprising a radioisotope of iodine.

12. The composition of claim 11, wherein the radioisotope I-125 or I-131.

13. A pharmaceutical composition comprising the composition of claims 1, 2, 3, 4, 5, 6, 7, 8, 9, or 10, and a pharmaceutically-acceptable carrier or excipient.

14. A method of performing radioisotope-guided surgery, or a radiodiagnostic or radiotherapeutic procedure using the composition of claim 11.

15. The composition of claims 1, 2, 5 or 8, wherein the somatostatin receptor-binding peptide is chemically synthesized in vitro.

16. The composition of claim 15, wherein the peptide is synthesized by solid phase peptide synthesis.

17. A method for alleviating a somatostatin-related disease in an animal comprising the step of administering a therapeutically effective amount of the composition of claims 1, 2, 3, 4, 5, 6, 7, 8, 9, or 10 to the animal.

18. The method of claim 17 wherein the animal is a human.

19. The composition of claim 1, wherein the sidechain of $C^4$ is covalently linked to an amino acid, an amino acid amide, or a peptide comprised of 2 to 10 amino acids.

20. A pharmaceutical composition comprising the composition of claim 11 and a pharmaceutically-acceptable carrier or excipient.

21. A pharmaceutical composition comprising the composition of claim 12 and a pharmaceutically-acceptable carrier or excipient.

22. A method for alleviating a somatostatin-related disease in an animal comprising the step of administering a therapeutically effective amount of the composition of claim 11 to the animal.

23. A method for alleviating a somatostatin-related disease in an animal comprising the step of administering a therapeutically effective amount of the composition of claim 12 to the animal.

* * * * *